United States Patent
Yamamoto

(10) Patent No.: US 9,895,134 B2
(45) Date of Patent: Feb. 20, 2018

(54) ULTRASOUND DIAGNOSTIC APPARATUS AND DATA PROCESSING METHOD

(71) Applicant: FUJIFILM Corporation, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 559 days.

(21) Appl. No.: 14/551,692

(22) Filed: Nov. 24, 2014

(65) Prior Publication Data

US 2015/0112198 A1   Apr. 23, 2015

Related U.S. Application Data

(63) Continuation of application No. PCT/JP2013/064458, filed on May 24, 2013.

(30) Foreign Application Priority Data

May 25, 2012   (JP) ................. 2012-120009

(51) Int. Cl.
| | |
|---|---|
| A61B 8/00 | (2006.01) |
| A61B 8/08 | (2006.01) |
| A61B 8/14 | (2006.01) |
| G01S 7/52 | (2006.01) |

(52) U.S. Cl.
CPC .............. *A61B 8/14* (2013.01); *A61B 8/4488* (2013.01); *A61B 8/469* (2013.01); *A61B 8/5207* (2013.01); *A61B 8/5269* (2013.01); *G01S 7/52049* (2013.01); *G01S 7/5205* (2013.01)

(58) Field of Classification Search
None
See application file for complete search history.

(56) References Cited

U.S. PATENT DOCUMENTS 4,214,269 A * 7/1980 Parker ................. G01S 7/531
                                                                342/185
4,627,291 A * 12/1986 Otsuki ................. G01S 15/06
                                                                73/634

(Continued)

FOREIGN PATENT DOCUMENTS

| JP | 7-262359 A | 10/1995 |
| JP | 2009-61086 A | 3/2009 |

(Continued)

OTHER PUBLICATIONS

Japanese Office Action dated Oct. 27, 2015, for Japanese Application No. 2012-120009 with a partial English translation.

(Continued)

*Primary Examiner* — Katherine Fernandez
*Assistant Examiner* — Bradley Impink
(74) *Attorney, Agent, or Firm* — Birch, Stewart, Kolasch & Birch, LLP

(57) ABSTRACT

There is provided an ultrasound diagnostic apparatus capable of outputting an appropriate ultrasound image with no distortion regardless of a sound velocity distribution in a subject. In the ultrasound diagnostic apparatus, sound velocities are calculated at two or more points in a subject, and coordinate transformation of a generated ultrasound image is performed based on the calculated sound velocities.

10 Claims, 10 Drawing Sheets

(56) References Cited

U.S. PATENT DOCUMENTS

| | | | | |
|---|---|---|---|---|
| 5,797,844 A * | 8/1998 | Yoshioka | ............ | G01S 7/52036 |
| | | | | 600/442 |
| 5,860,925 A * | 1/1999 | Liu | ....................... | G01S 7/5206 |
| | | | | 348/442 |
| 5,902,244 A * | 5/1999 | Kobayashi | .......... | G01S 7/52044 |
| | | | | 600/445 |
| 6,315,731 B1 * | 11/2001 | Okuno | ................ | G01S 7/52023 |
| | | | | 600/447 |
| 2009/0292207 A1 * | 11/2009 | Karasawa | ................ | A61B 8/14 |
| | | | | 600/447 |
| 2011/0077519 A1 * | 3/2011 | Katsuyama | .............. | A61B 8/08 |
| | | | | 600/443 |

FOREIGN PATENT DOCUMENTS

| | | |
|---|---|---|
| JP | 2009-100997 A | 5/2009 |
| JP | 2009-279306 A | 12/2009 |
| JP | 2011-92686 A | 5/2011 |

OTHER PUBLICATIONS

International Preliminary Report on Patentability and translation of the Written Opinion of the International Searching Authority (Forms PCT/IB/338, PCT/IB/373 and PCT/ISA/237), dated Dec. 4, 2014, in International Application No. PCT/JP2013/064458.
International Search Report, issued in PCT/JP2013/064458, dated Aug. 27, 2013.

* cited by examiner

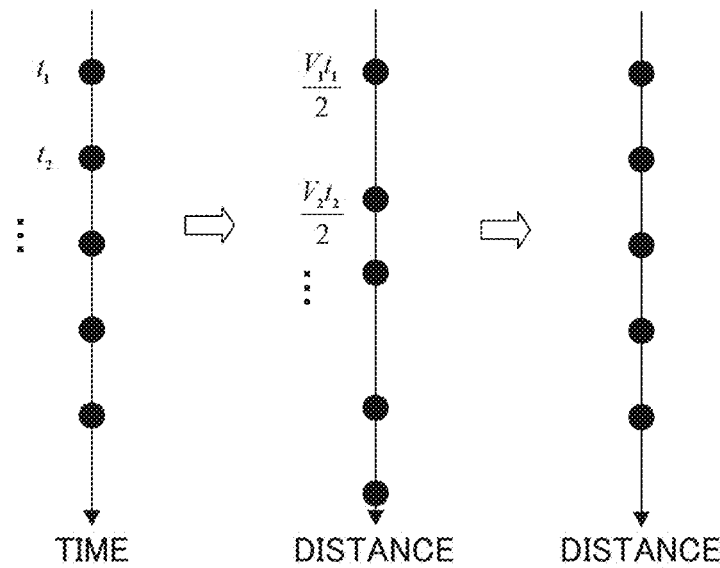
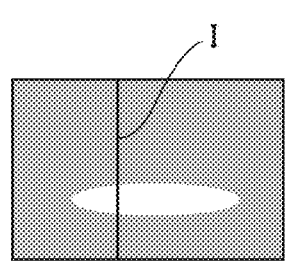
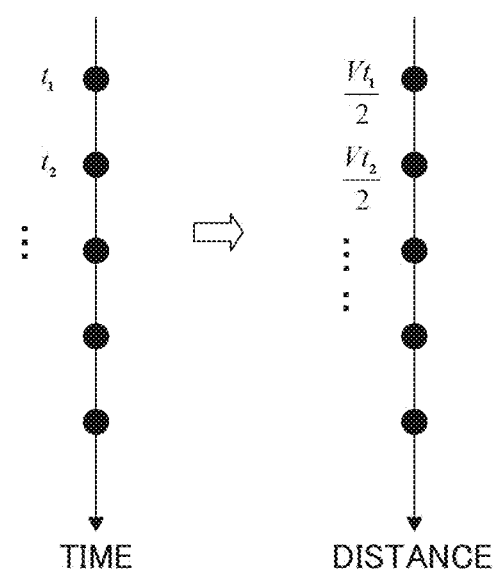

ULTRASOUND DIAGNOSTIC APPARATUS AND DATA PROCESSING METHOD

CROSS REFERENCE TO RELATED APPLICATIONS

This application is a continuation application of International Application No. PCT/JP2013/064458 filed on May 24, 2013, which claims priority under 35 U.S.C. 119(a) to Patent Application No. 2012-120009 filed in Japan on May 25, 2012, all of which are hereby expressly incorporated by reference into the present application.

BACKGROUND OF THE INVENTION

The present invention relates to an ultrasound diagnostic apparatus and a method for processing data of ultrasonic echoes, particularly to an ultrasound diagnostic apparatus and data processing method capable of obtaining high-quality image regardless of the difference in sound velocity in a subject's body.

Ultrasound diagnostic apparatuses using ultrasound images are put to practical use in the medical field.

Generally, an ultrasound diagnostic apparatus of this type comprises an ultrasound probe (hereinafter called "probe") and a diagnostic apparatus body. In such an ultrasound diagnostic apparatus, a probe transmits an ultrasonic wave toward a subject's body, the ultrasonic echo from the subject is received by the probe, and the resulting reception signals are electrically processed by a diagnostic apparatus body to generate an ultrasound image.

In conventional ultrasound diagnostic apparatuses, the sound velocity of ultrasonic waves is assumed to be constant in a living body of a subject, and a sound velocity value of ultrasonic waves is fixed to a certain value.

However, the sound velocity varies depending on the type of tissues of a fatty layer, a muscular layer and the like, and therefore the sound velocity of ultrasonic waves is not constant in a subject. Further, fat people and slim people are different in thickness of a fatty layer and a muscular layer. In other words, the sound velocity varies from person to person.

Accordingly, in the case of a conventional ultrasound diagnostic apparatus in which the sound velocity of ultrasonic waves is fixed, when the actual sound velocity in a subject differs from a set sound velocity, the arrival time of an ultrasonic echo reflected inside the subject does not match with a set delay time.

This hinders appropriate phase matching, and reception focusing is not properly performed, so that the image quality of the resulting ultrasound image deteriorates. In addition, there is a problem in that the resulting ultrasound image is distorted relative to the actual subject.

To cope with such a problem, JP 2011-92686 A describes an ultrasound diagnostic apparatus that sets a region of interest, transmits and receives ultrasonic waves, calculates a focus index, which is brightness for instance, for each of plural, appropriately set sound velocities by performing reception focusing on an acquired reception signal with the use of the sound velocities, and determines a sound velocity at the region of interest using the calculated focus index, for instance, determines a set sound velocity with the highest brightness, which is the focus index, as the sound velocity at the region of interest.

In the ultrasound diagnostic apparatus described in JP 2011-92686 A, as an example, the delay time and delay pattern is adjusted based on the determined sound velocity before the reception focusing is performed and an ultrasound image is generated. Thus, the ultrasound diagnostic apparatus is capable of steadily outputting an appropriate ultrasound image regardless of the difference in sound velocity inside a subject or among subjects.

JP 2009-100997 A describes an ultrasound diagnostic apparatus that uses the facts that the intensity of a reception signal (echo intensity) reflects the hardness of tissue at a reflection point in a subject and that a sonic speed varies depending on the hardness of tissue, thereby preventing the image quality from deteriorating due to the difference in sonic speed inside a subject.

When this ultrasound diagnostic apparatus is used, on the basis of the facts that the intensity of a reception signal can be an index of hardness of tissue and that the hardness of tissue and the sonic speed are correlated with each other to some extent, a ratio table indicative of the relation between the intensity of a reception signal and a sonic speed ratio, which is a variation of sonic speed relative to a set sonic speed, is prepared in advance. Thereafter, the sonic speed ratio is detected using the intensity of reception based on the ratio table, and pixel positions in an ultrasound image are rearranged using the sonic speed ratio to thereby perform sonic speed correction.

SUMMARY OF THE INVENTION

However, only by determining the sound velocity in a subject and performing the reception focusing based on the determined sound velocity as described in JP 2011-92686 A, the deterioration in image quality of ultrasound images caused by, for example, the sound velocity that varies in a subject is not sufficiently prevented.

Besides, the intensity of a reception signal and the hardness of tissue do not necessarily have a certain correlation. Hence, appropriate sonic speed correction may occasionally not be implemented through the processing described in JP 2009-100997 A, possibly resulting in a distorted ultrasound image.

An object of the present invention is to solve the foregoing problems of the prior art and to provide an ultrasound diagnostic apparatus and data processing method capable of generating a high-quality ultrasound image which is not adversely affected in terms of image quality by the difference in sound velocity inside a subject.

In order to attain the above object, the present invention provides an ultrasound diagnostic apparatus, comprising: an ultrasound probe having ultrasound transducers each adapted to transmit an ultrasonic wave, receive an ultrasonic echo reflected by a subject and output an analog reception signal in accordance with the ultrasonic echo as received; an analog-to-digital converter adapted to analog-to-digital convert the analog reception signal output by each of the ultrasound transducers into a digital reception signal; a storage adapted to store the digital reception signal; a sound velocity determiner adapted to determine a sound velocity at each of plural points in the subject by using the digital reception signal converted from the analog reception signal by the analog-to-digital converter or the digital reception signal read out from the storage; a signal processor adapted to generate a brightness image of the subject by at least performing reception focusing processing on the digital reception signal converted from the analog reception signal by the analog-to-digital converter or the digital reception signal read out from the storage; and a coordinate transformer adapted to perform coordinate transformation on the brightness image generated by the signal processor based on the sound velocity determined by the sound velocity determiner.

In the ultrasound diagnostic apparatus of the invention, preferably, the coordinate transformation performed by the coordinate transformer allows time-distance conversion.

Preferably, the coordinate transformer performs interpolation on pixels in a brightness image having undergone the coordinate transformation to thereby generate a corrected image having pixel positions corresponding to those of a brightness image not yet undergoing the coordinate transformation.

Preferably, the ultrasound diagnostic apparatus further comprises a region-of-concern setter adapted to set at least one region of concern; and a transmission and reception controller adapted to cause the ultrasound probe to transmit and receive ultrasonic waves such that the ultrasonic waves correspond to the region of concern as set, wherein the sound velocity determiner includes a set sound velocity specifying section adapted to set a plurality of set sound velocities for use in performing reception focusing on a digital reception signal the region of concern; and a focus index calculating section adapted to calculate a focus index of a brightness image at the region of concern by performing the reception focusing on a digital reception signal of the region of concern for each of the plurality of set sound velocities, and determines a sound velocity at the region of concern using the focus index.

Preferably, the signal processor performs the reception focusing processing using the sound velocity calculated by the sound velocity determiner.

Preferably, the region-of-concern setter sets regions of concern at least either at two or more points in a depth direction or at two or more points in an azimuth direction.

Preferably, the region-of-concern setter sets two or more regions of concern, and the sound velocity determiner determines a sound velocity at each of two or more of the regions of concern set by the region-of-concern setter.

Preferably, the sound velocity determiner determines a sound velocity corresponding to each of all pixels of the brightness image generated by the signal processor The present invention further provides a data processing method, comprising: a step of obtaining an analog reception signal corresponding to an ultrasonic echo reflected by a subject by transmitting an ultrasonic wave to the subject; a step of analog-to-digital converting the analog reception signal into a digital reception signal; a step of storing the digital reception signal; a step of determining a sound velocity at each of plural points in the subject by using the digital reception signal as analog-to-digital converted or the digital reception signal as stored; a step of generating a brightness image of the subject by at least performing reception focusing processing on the digital reception signal as analog-to-digital converted or the digital reception signal as stored; and a step of performing coordinate transformation on the brightness image as generated based on the sound velocity as determined.

In the data processing method of the invention, preferably, the coordinate transformation allows time-distance conversion.

Preferably, the data processing method includes a step of generating a corrected image having pixel position corresponding to a brightness image not yet undergoing the coordinate transformation by performing interpolation on pixels in a brightness image having undergone the coordinate transformation.

Preferably, the data processing method includes a step of setting at least one region of concern and transmitting and receiving ultrasonic waves such that the ultrasonic waves correspond to the region of concern as set, wherein in the step of determining a sound velocity, a plurality of set sound velocities are set for use in performing reception focusing on a digital reception signal of the region of concern, a focus index of a brightness image at the region of concern is calculated by performing the reception focusing on a digital reception signal of the region of concern for each of the plurality of set sound velocities, and a sound velocity at the region of concern is determined using the focus index.

Preferably, in the step of generating a brightness image of the subject, the reception focusing processing is performed using the sound velocity as determined.

Preferably, in the step of setting at least one region of concern, regions of concern are set at least either at two or more points in a depth direction or at two or more points in an azimuth direction.

Preferably, in the step of setting at least one region of concern, two or more regions of concern are set, and in the step of determining a sound velocity, a sound velocity is determined at each of two or more of the regions of concern as set.

Preferably, in the step of determining a sound velocity, a sound velocity corresponding to each of all pixels of the brightness image as generated is determined.

According to the present invention, sound velocities are determined at two or more points in a subject, and coordinate transformation of an ultrasound image generated from reception signals is performed using the sound velocities, whereby it is possible to generate a high-quality ultrasound image in which distortion of the image caused by the difference in sound velocity in the subject, i.e., a sound velocity distribution in the subject, has been corrected.

In addition, since a reception signal which is obtained by A/D converting an analog reception signal output by an ultrasound probe (ultrasound transducer) and is not yet subjected to reception focusing (phase matching addition) is stored, the reception signal can be used to accurately determine a sound velocity.

BRIEF DESCRIPTION OF THE DRAWINGS

FIGS. 10A to 10C are conceptual diagrams for explaining distortion correction in the ultrasound diagnostic apparatus shown in FIG. 1.

FIGS. 11A to 11C are conceptual diagrams for explaining generation of a B-mode image in a general ultrasound diagnostic apparatus.

DETAILED DESCRIPTION OF THE INVENTION

An ultrasound diagnostic apparatus and data processing method of the present invention are described in detail below with reference to a preferred embodiment shown in the accompanying drawings.

Figure 1:
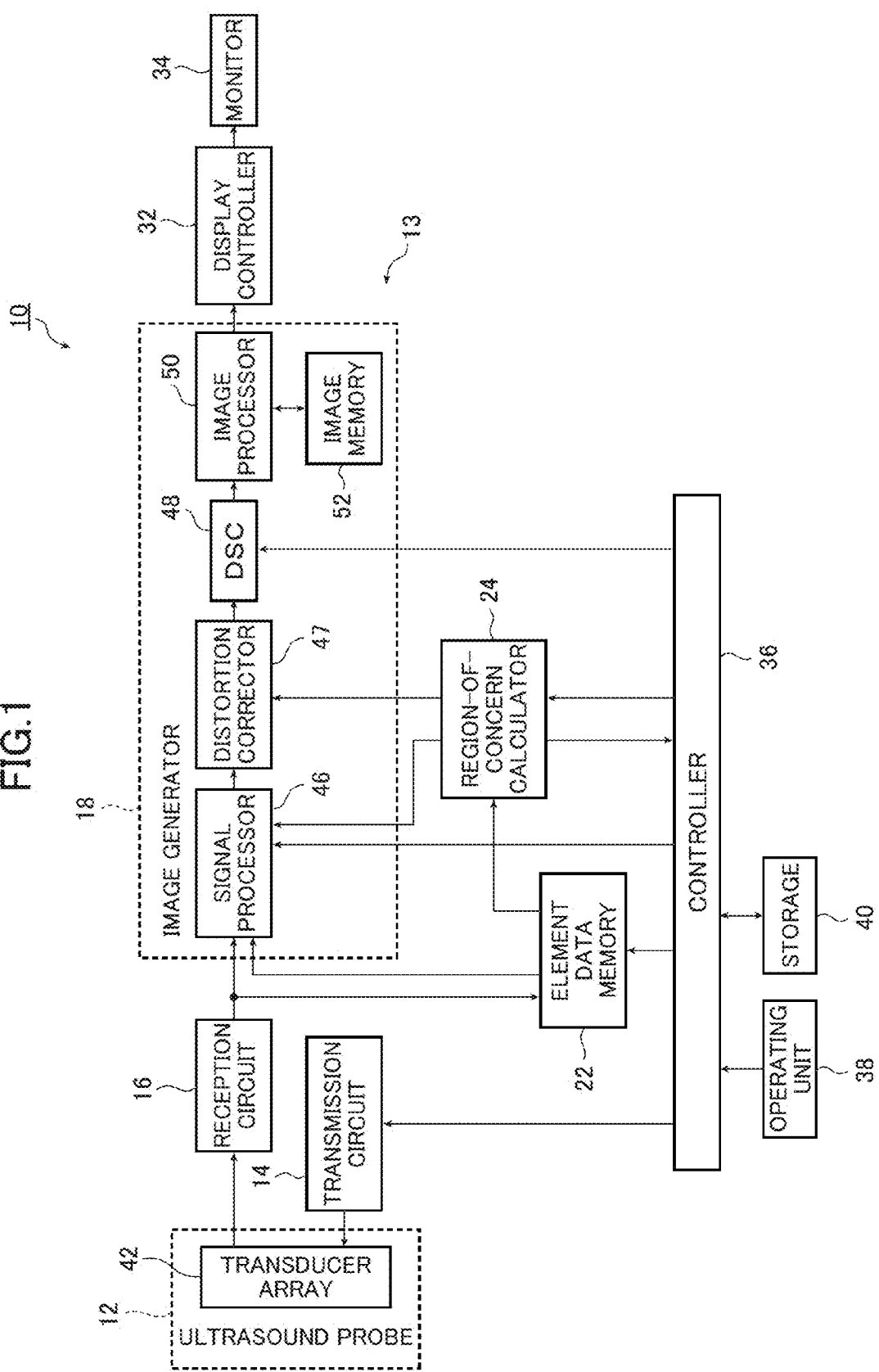
FIG. 1 is a block diagram showing the configuration of an embodiment of an ultrasound diagnostic apparatus of the invention that implements a data processing method of the invention.

FIG. 1 is a block diagram conceptually showing an example of the ultrasound diagnostic apparatus of the invention that implements the data processing method of the invention.

An ultrasound diagnostic apparatus 10 shown in FIG. 1 includes an ultrasound probe 12 and a diagnostic apparatus body 13 connected to the ultrasound probe 12 as with general ultrasound diagnostic apparatuses.

In the ultrasound diagnostic apparatus 10, the ultrasound probe 12 transmits an ultrasonic beam toward a subject and outputs a reception signal, which has been generated based on an ultrasonic echo reflected by the subject, to the diagnostic apparatus body 13, while the diagnostic apparatus body 13 processes the reception signal to generate and display an ultrasound image.

The ultrasound probe 12 is held in contact with the subject in use and includes a transducer array 42 of type used in general ultrasound diagnostic apparatuses.

The transducer array 42 includes a plurality of ultrasound transducers (ultrasound transmission and reception elements) arranged one-dimensionally or two-dimensionally. When an ultrasound image is taken, the ultrasound transducers transmit ultrasonic beams to the subject in accordance with driving signals supplied from a transmission circuit 14 to them, respectively, and output reception signals corresponding to ultrasonic echoes which have been reflected by the subject.

Each of the ultrasound transducers comprises an oscillator composed of a piezoelectric body and electrodes each provided on either end of the piezoelectric body. The piezoelectric body is composed of, for example, a piezoelectric ceramic represented by a PZT (lead zirconate titanate), a piezoelectric polymer represented by PVDF (polyvinylidene fluoride), or a piezoelectric monocrystal represented by PMN-PT (lead magnesium niobate-lead titanate solid solution).

When a pulsed voltage or a continuous-wave voltage is applied across the electrodes of such an oscillator, the piezoelectric body expands and contracts in response to the applied voltage and the oscillator generates pulsed or continuous ultrasonic waves. Ultrasonic waves generated from the oscillators are combined based on the delay of operation of the individual oscillators, thereby forming an ultrasonic beam. In other words, transmission focusing is performed on ultrasonic waves generated from the oscillators to form ah ultrasonic beam.

When an ultrasonic echo having been reflected inside the subject enters the oscillator, the oscillator expands and contracts in response to the ultrasonic echo and generates an electric signal corresponding to the magnitude of the expansion and contraction. The electric signal is output as an analog reception signal to a reception circuit 16 of the diagnostic apparatus body 13.

The diagnostic apparatus body 13 (hereinafter called "apparatus body 13") includes the transmission circuit 14, the reception circuit 16, an image generator 18, an element data memory 22, a region-of-concern calculator 24, a display controller 32, a monitor 34, a controller 36, an operating unit 38 and a storage 40.

The transmission circuit 14 has, for example, a plurality of pulsers and supplies driving signals to the ultrasound transducers of the transducer array 42 of the ultrasound probe 12. The supply of a driving signal means, for instance, the application of a driving voltage.

The transmission circuit 14 performs the transmission focusing for modifying delay amounts of driving signals (timings of application of driving voltages) based on a transmission delay pattern selected by the controller 36 so that ultrasonic waves transmitted by the ultrasound transducers form a desired ultrasonic beam, and supplies the driving signals to the ultrasound transducers. Consequently, the ultrasound probe 12 (transducer array 42) transmits a desired ultrasonic beam to the subject.

The reception circuit 16 amplifies and analog-to-digital (A/D) converts the analog reception signals transmitted from the respective ultrasonic transducers of the transducer array 42 to generate digital reception signals (RF data). Hereinafter, the digital reception signals generated by the reception circuit 16 are also referred to as "element data."

The reception circuit 16 supplies the generated element data to the image generator 18 and the element data memory 22.

As described above, the transmission of ultrasonic waves is performed in accordance with the transmission delay pattern. In addition, when an ambient sound velocity to be described later has not been determined yet, the processing of element data (reception signals), i.e., the generation of an ultrasound image in a signal processor 46 to be described later is performed in accordance with a reception delay pattern.

The transmission delay pattern is pattern data on delay times to be given to driving signals for the purpose of forming an ultrasonic beam in a desired direction with ultrasonic waves transmitted from the ultrasound transducers. On the other hand, the reception delay pattern is pattern data on delay times to be given to element data for the purpose of extracting an ultrasonic echo coming from a desired direction from ultrasonic waves received by the ultrasound transducers.

A plurality of transmission delay patterns and a plurality of reception delay patterns are stored in the storage 40 in advance. The controller 36 selects a transmission delay pattern and a reception delay pattern from among the transmission delay patterns and reception delay patterns stored in the storage 40 and outputs control signals to the transmission circuit 14 and the signal processor 46 in accordance with the selected transmission delay pattern and reception delay pattern to thereby control the transmission and reception of ultrasonic waves.

The image generator 18 generates an ultrasound image from the element data (reception signals) supplied from the reception circuit 16.

As shown in FIG. 1, the image generator 18 includes the signal processor 46, a distortion corrector 47, a digital scan converter (DSC) 48, an image processor 50 and an image memory 52.

A distance between an ultrasonic wave reflection source in the subject and each ultrasound transducer varies among the ultrasound transducers. Therefore, even when ultrasonic waves are reflected on the same reflection source, the arrival time of an ultrasonic echo at each ultrasound transducer varies.

The signal processor 46 performs the reception focusing processing by correcting the difference in arrival time, i.e., delay time, of ultrasonic echoes in reception data for a brightness image based on a control signal corresponding to the reception delay pattern supplied from the controller 36 or an ambient sound velocity supplied from the region-of-concern calculator 24 to be described later, and also performs further predetermined processing to thereby generate an ultrasound image (B-mode image signal).

In this embodiment, the signal processor 46 delays each piece of reception data by an amount corresponding to the delay time of an ultrasonic echo for each ultrasound transducer and performs matching addition on the pieces of reception data each provided with the delay time, thereby digitally performing the reception focusing processing.

As an example, the ultrasound diagnostic apparatus 10 is configured to be able to select one of (switch between) the reception focusing processing corresponding to reception delay pattern and the reception focusing processing corresponding to ambient sound velocity depending on, for instance, the mode.

When the reception focusing processing corresponding to ambient sound velocity is selected as a result of the selection of the mode or the like, upon storage of element data into the element data memory 22, the ultrasound diagnostic apparatus 10 reads out the element data from the element data memory 22 to determine an ambient sound velocity and corrects the delay time with the ambient sound velocity by a method shown in FIG. 2, which will be described later, to thereby perform the reception focusing processing. The determination of the ambient sound velocity will be described later in detail. When the reception focusing processing corresponding to ambient sound velocity is selected, the ultrasound diagnostic apparatus 10 also performs distortion correction through coordinate transformation using the ambient sound velocity, which will be described later. In other words, when a distortion correction mode to be described later is selected, the ultrasound diagnostic apparatus 10 also performs distortion correction through coordinate transformation using the ambient sound velocity, which will be described later.

The present invention may be configured so that whether to perform the distortion correction when the reception focusing processing corresponding to ambient sound velocity is selected is also selectable depending on the mode or the like.

On the other hand, when the reception focusing processing corresponding to reception delay pattern is selected as a result of the selection of the mode or the like, the signal processor 46 performs the reception focusing processing in accordance with the reception delay pattern as with known ultrasound diagnostic apparatuses.

In the present invention, however, the reception focusing is not limited to the foregoing example and various methods of the reception focusing are applicable.

For instance, the ultrasound diagnostic apparatus may perform the reception focusing processing corresponding to reception delay pattern before the operator sets a region of interest (ROI) as with known ultrasound diagnostic apparatuses, and once the ROI is set, determine the ambient sound velocity and from then on, correct the delay time by the method shown in FIG. 2 to be described later, thereby performing the reception focusing processing.

Further, in the present invention, the reception focusing processing corresponding to ambient sound velocity is not limited to the foregoing method.

For instance, the controller 36 may select the reception delay pattern corresponding to ambient sound velocity and supply to the signal processor 46 a control signal corresponding to the selected reception delay pattern. Alternatively, the controller 36 may correct the reception delay pattern based on the ambient sound velocity and supply to the signal processor 46 a control signal corresponding to the corrected reception delay pattern. Still alternatively, the signal processor 46 may correct a control signal supplied from the controller 36 in accordance with the ambient sound velocity to thereby perform the reception focusing processing.

When other ultrasonic wave reflection sources are present at positions different from the position where the above ultrasonic wave reflection source is present, since reception signals from the other ultrasonic wave reflection sources differ in arrival time, the signal processor 46 performs an addition to cause phases of the reception signals from the other ultrasonic wave reflection sources to cancel each other. As a result, a reception signal from the ultrasonic wave reflection source is to be the largest, and the reception signal comes into focus. This reception focusing processing yields reception data (sound ray signals) having the ultrasonic echoes well focused.

As described above, the reception focusing processing using the reception delay pattern may be performed as with known ultrasound diagnostic apparatuses.

On the other hand, the reception focusing processing corresponding to ambient sound velocity is performed by correcting the delay time of element data (reception signals) in accordance with the ambient sound velocity. The correction on the delay time of element reception data by the signal processor 46 is described below.

Figure 2:
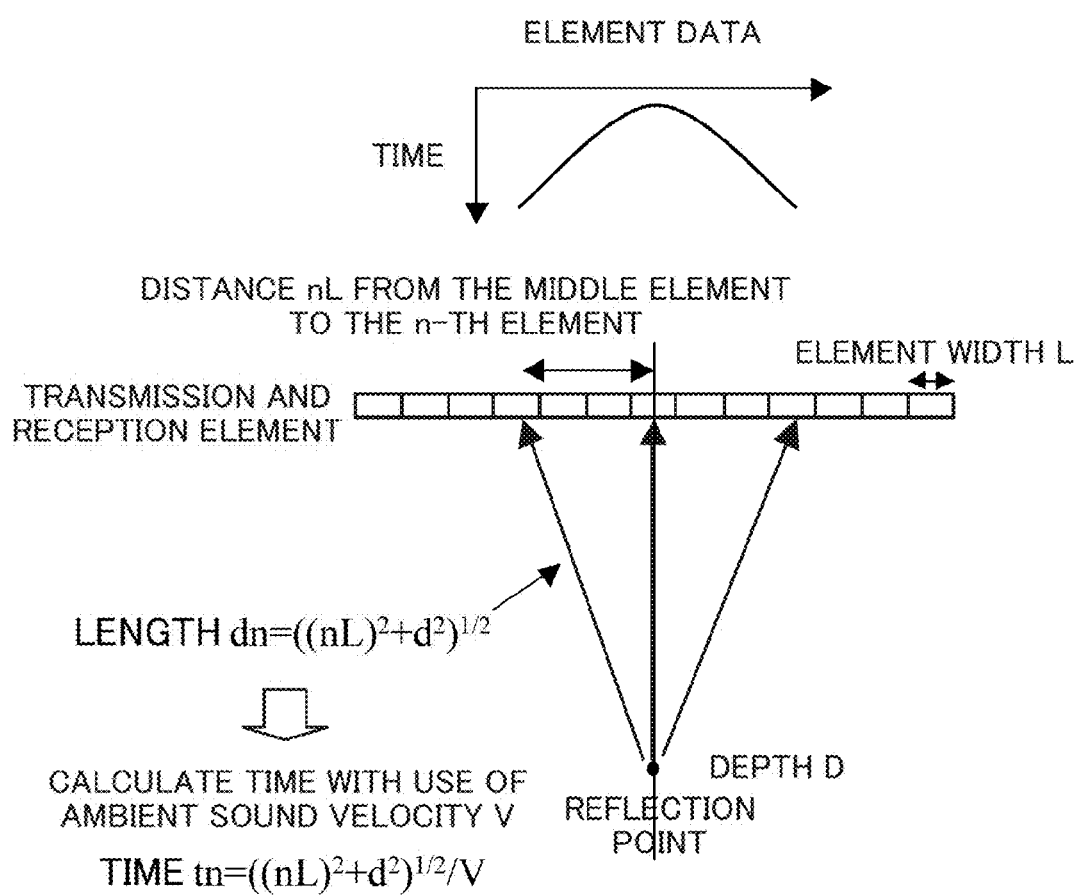
FIG. 2 is a conceptual diagram for explaining a method of correcting a delay time of reception data based on an ambient sound velocity.

FIG. 2 is a conceptual diagram showing the correction on the delay time of element data based on the ambient sound velocity. In this example, as shown in FIG. 2, the ultrasound transducers (ultrasound transmission and reception elements) in the ultrasound probe 12 are arranged in a single line in the lateral direction in the drawing.

The width of each of the ultrasound transducers is assumed to be L in the direction in which the ultrasound transducers are arranged (azimuth direction). Therefore, the distance from the middle ultrasound transducer to the n-th ultrasound transducer toward either end in the arrangement direction is to be nL.

As shown in the drawing, a reflection point of an ultrasonic wave is assumed to be positioned at a distance (depth) d from the middle ultrasound transducer as measured in a direction perpendicular to the arrangement direction. In this case, the distance (length) $d_n$ between the n-th ultrasound transducer and the reflection point is calculated by Equation (1).

$$d_n = ((nL)^2 + d^2)^{1/2} \tag{1}$$

Accordingly, the time $t_n$ taken for an ultrasonic wave to travel from the reflection point to the n-th ultrasound transducer is calculated using an ambient sound velocity V by Equation (2).

$$t_n = d_n/V = ((nL)^2 + d^2)^{1/2}/V \tag{2}$$

Thus, the distance between each ultrasound transducer and the reflection point varies among the ultrasound transducers. In this example, the time $t_n$ increases as an ultrasound transducer is positioned closer to either end in the arrangement direction, as can be seen from the graph at the top of the drawing.

To be more specific, in the case of an ultrasonic wave received by the n-th ultrasound transducer, when the time taken for an ultrasonic wave to travel from the reflection point to the middle ultrasound transducer is assumed to be t1, the arrival time of the ultrasound wave at the n-th ultrasound transducer is delayed by the time $\Delta t = t_n - t_1$ compared to the ultrasonic wave received by the middle ultrasonic transducer. The signal processor 46 corrects the delay time expressed by the time $\Delta t$ as above for respective pieces of reception data corresponding to the individual ultrasound transducers. This delay time $\Delta t$ is called "reception delay pattern." As described above, the delay time $\Delta t$ of each piece of reception data is calculated from the distance and ambient sound velocity which are determined from geometric arrangement of the reflection point and each ultrasound transducer.

While the ultrasound probe 12 is a linear probe in the foregoing example, the same concept can be applied to a convex probe because there is a difference only in probe shape.

Furthermore, the signal processor 46 performs predetermined data processing on the element data having undergone the reception focusing processing.

In this embodiment, the signal processor 46 performs correction for the attenuation, which is caused due to distance, based on the depth at which the ultrasonic waves are reflected and then performs an envelope detection process to thereby generate a B-mode image (B-mode image signal) that is tomographic image information related to tissue in the subject. As is known, the B-mode image is a brightness image (image signal) showing the amplitude of ultrasonic echoes using the brightness of points.

The distortion corrector 47 corrects distortion in the B-mode image generated by the signal processor 46 in accordance with the ambient sound velocity supplied from the region-of-concern calculator 24.

As described above, once the ambient sound velocity is determined, the signal processor 46 performs the reception focusing processing corresponding to ambient sound velocity to generate a B-mode image. However, the ambient sound velocity often varies depending on the position inside the subject. In other words, the subject has in its inside a sound velocity distribution. More specifically, the arrival time of an ultrasonic echo from the reflection point to an ultrasound transducer varies depending on the ambient sound velocity at a position in the subject.

Therefore, even when the reception focusing processing corresponding to ambient sound velocity is performed, the position of each pixel of a B-mode image does not match the actual position in the subject. That is, the sound velocity distribution in the subject causes the resulting image to have distortion.

To deal with it, in the present invention, the distortion corrector 47 performs coordinate transformation based on the ambient sound velocity in the subject, thereby achieving the generation of a B-mode image with no distortion.

The distortion corrector 47 first performs coordinate transformation on the B-mode image generated by the signal processor 46 in accordance with ambient sound velocities at two or more points in the subject that have been determined by the region-of-concern calculator 24. Specifically, in this embodiment, the distortion corrector 47 rearranges pixels of the B-mode image generated by the signal processor 46 in accordance with ambient sound velocities at two or more regions of concern among regions of concern to be described later.

Subsequently, the distortion corrector 47 generates a pixel signal of a predetermined pixel position by interpolation, generates a B-mode image having undergone the distortion correction and supplies the B-mode image to the DSC 48.

The distortion corrector 47 will be described later in detail.

As will be detailed later, in this embodiment, the ambient sound velocity is determined after a region of concern to be described later is set.

Therefore, the signal processor 46 performs the reception focusing processing not based on the ambient sound velocity but based on a control signal corresponding to the reception delay pattern until a region of concern is set, i.e., the ambient sound velocity is determined. Besides, the distortion corrector 47 to be described later does not perform the distortion correction on a B-mode image (ultrasound image) until a region of concern is set, i.e., the ambient sound velocity is determined.

The B-mode image generated by the signal processor 46 and having undergone the distortion correction performed by the distortion corrector 47 is an image obtained through a scanning method different from a general television signal scanning method.

Accordingly, the DSC 48 converts the B-mode image signal generated by the signal processor 46 into a general image signal under the control of the controller 36. As an example, the DSC 48 converts the B-mode image signal into an image signal compatible with a television signal scanning mode (raster conversion). The television signal scanning mode is, for instance, a National Television System Committee (NTSC) method.

The image processor 50 performs various types of necessary image processing including gradation processing on the B-mode image signal entered from the DSC 48, and then outputs the B-mode image signal having undergone such image processing to the display controller 32 while storing the B-mode image signal in the image memory 52.

The display controller 32 causes the monitor 34 to display an ultrasound diagnostic image based on the B-mode image signal having undergone image processing performed by the image processor 50.

The monitor 34 comprises a display device such as an LCD, for example, and displays an ultrasound diagnostic image (moving image/ still image), various setting screens and the like under the control of the display controller 32.

The element data memory 22 sequentially stores the element data (digital reception signals) supplied from the reception circuit 16. The element data memory 22 also stores information on a frame rate entered from the controller 36 in association with the above element data. The information on a frame rate includes, for example, the depth of a position at which an ultrasonic wave is reflected, the density of scanning lines, and a parameter representing the range of visual field.

The element data and the information on a frame rate stored in the element data memory 22 are supplied to the signal processor 46 and the region-of-concern calculator 24.

The region-of-concern calculator 24 analyzes the element data to calculate ambient sound velocities at two or more points in the subject. Preferably, the region-of-concern calculator 24 calculates ambient sound velocities at two or more regions of concern to be described later.

In this embodiment, the region-of-concern calculator 24 sets at least one region of concern and reads out the element data (digital reception signals) of the set region of concern from the element data memory 22, which will be described later. Furthermore, the region-of-concern calculator 24 performs the reception focusing processing on the element data to calculate a focus index and determines an ambient sound velocity at the region of concern using the focus index.

The region-of-concern calculator 24 outputs the calculated ambient sound velocity to the signal processor 46 and the distortion corrector 47.

In the present invention, a region of concern is not limited to the one set by the region-of-concern calculator 24. Plural positions (regions) set in advance, plural positions input by the operator as desired or the like may be processed as regions of concern in the same manner as a region of concern to be described later.

The region-of-concern calculator 24 sets preferably two or more regions of concern, and more preferably two or more regions of concern in the depth direction (transmission and reception direction of ultrasonic waves) and/or two or more regions of concern in the azimuth direction.

Furthermore, the region-of-concern calculator 24 determines sound velocities preferably at two or more regions of concern among the set regions of concern, more preferably at two or more regions of concern in the depth direction and/or two or more regions of concern in the azimuth direction, and still more preferably at each of the regions of concern. Most preferably, the region-of-concern calculator 24 sets regions of concern so that the regions of concern respectively correspond to all pixels of a B-mode image and determines sound velocities corresponding to all the respective pixels of the B-mode image.

The controller 36 controls the components in the ultrasound diagnostic apparatus 10 in accordance with instructions entered through the operating unit 38 by the operator such as a medical doctor. The controller 36 selects a transmission delay pattern and reception delay pattern from among the transmission delay patterns and reception delay patterns stored in the storage 40 and outputs control signals to the transmission circuit 14 and the signal processor 46 in accordance with the selected patterns to thereby control the transmission and reception of ultrasonic waves.

The operating unit 38 is an input device used to enter instructions from the operator and may be composed of, for example, a keyboard, a mouse, a track ball, and/or a touch panel.

The storage 40 stores operation programs for the controller 36 to control the components in the ultrasound diagnostic apparatus 10, the transmission delay patterns, the reception delay patterns and the like, and may be constituted by a recording medium such as a hard disk, a flexible disk, an MO, an MT, a RAM, a CD-ROM and a DVD-ROM.

The signal processor 46, the DSC 48, the image processor 50, the display controller 32 and the region-of-concern calculator 24 are constituted by a CPU (computer) and operation programs for causing the CPU to perform various kinds of processing, but they may be constituted by a digital circuitry.

Next, the region-of-concern calculator 24 is described in detail.

Figure 3:
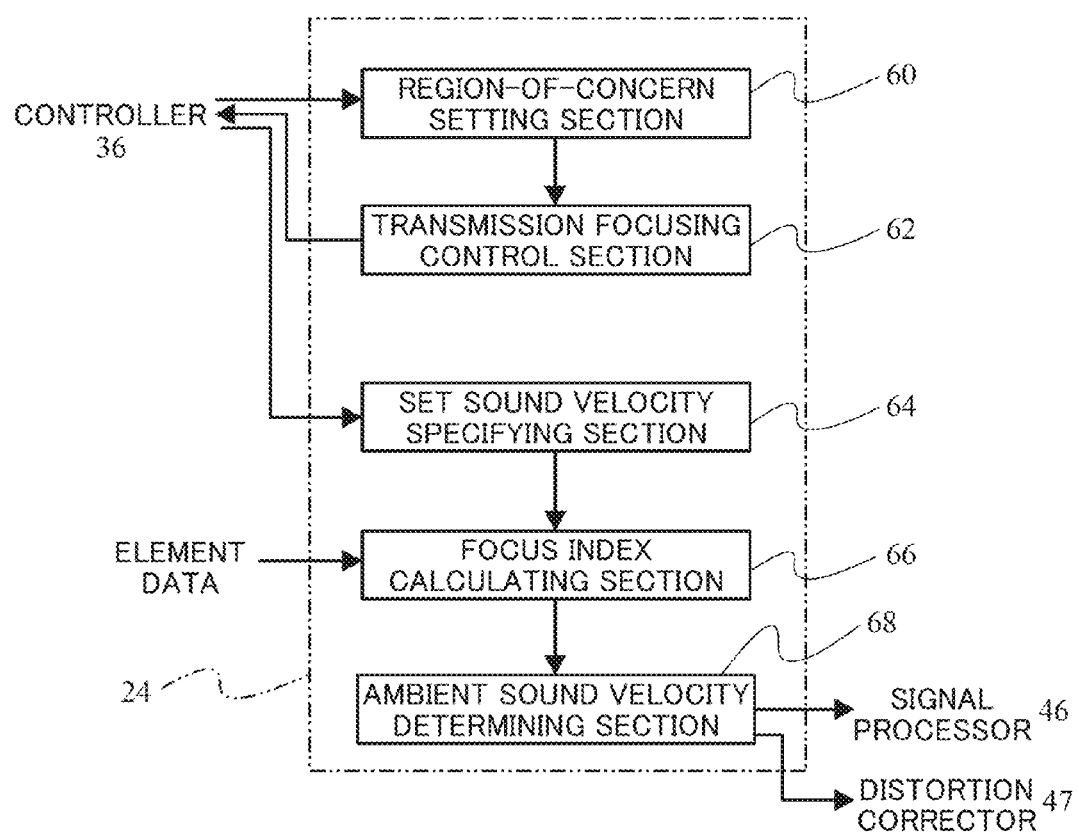
FIG. 3 is a block diagram conceptually showing the configuration of a region-of-concern calculator shown in FIG. 1.

FIG. 3 is a block diagram showing the configuration of the region-of-concern calculator shown in FIG. 1.

As shown in FIG. 3, the region-of-concern calculator 24 includes a region-of-concern setting section 60, a transmission focusing control section 62, a set sound velocity specifying section 64, a focus index calculating section 66 and an ambient sound velocity determining section 68.

The region-of-concern setting section 60 sets a region of concern on a B-mode image (ultrasound image) in accordance with an instruction from the controller 36.

In this embodiment, the region-of-concern setting section 60 divides the whole display of the B-mode image into a grid pattern and set each of the resulting segments as a region of concern. The number of the segments resulting from the division may be set in advance as a default value, or may be set to any value in the azimuth direction and/or depth direction by the operator. In the case where the number of the segments is set by default, a set value may vary depending on the image size or the site to be observed. Several options of the number of the segments may be set in advance so that the operator can choose.

Alternatively, not the whole display but a part thereof which has been set in advance or chosen from plural options may be divided in a grid pattern and each of the resulting segments may be set as a region of concern. Still alternatively, regions of concern may be set not for the whole display but for the ROI set by the operator. Even when regions of concern are set for a part of the display or the ROI, the division may be carried out in the same manner as that for the whole display. The operator may choose whether to set regions of concern for the whole display or the ROI.

The division is not necessarily carried out to result in a grid pattern. When a B-mode image has a fan-like shape as in an ultrasound image generated with a convex probe, the B-mode image may be divided into segments of fan-like shape accordingly. Also in this case, it is preferable to set not one but two or more regions of concern.

In any case, it is preferable to set two or more regions of concern, and more preferable to set two or more regions of concern in the depth direction and/or two or more regions of concern in the azimuth direction, as described above.

In the case where an image greatly varies or where an observation condition such as observation magnification and observation depth is modified, or in other cases, a region of concern may be changed or updated, and such change or update of a region of concern may be carried out as instructed by the operator. The case where an image greatly varies described above refers to the case where a variation in the amount of image characteristics exceeds a threshold value.

The transmission focusing control section 62 gives a transmission focusing instruction to the controller 36 so that the transmission circuit 14 performs the transmission focusing for the set region of concern.

The set sound velocity specifying section 64 specifies set sound velocities for use in the reception focusing on reception data in determining an ambient sound velocity under the control of the controller 36.

The focus index calculating section 66 reads out reception data of a region of concern from the element data memory 22 and performs the reception focusing on the reception data for each of the plural set sound velocities specified by the set sound velocity specifying section 64 to thereby calculate a focus index of the reception data.

The ambient sound velocity determining section 68 determines the ambient sound velocity of a region of concern based on the focus index for each of the plural set sound velocities.

As described above, in the present invention, it is preferable to determine sound velocities at two or more regions of concern among the set regions of concern, and more preferable to determine sound velocities at two or more regions of concern in the depth direction and/or two or more regions of concern in the azimuth direction. In this embodiment, it is particularly preferable to determine ambient sound velocities for each of the set regions of concern.

Figure 4:
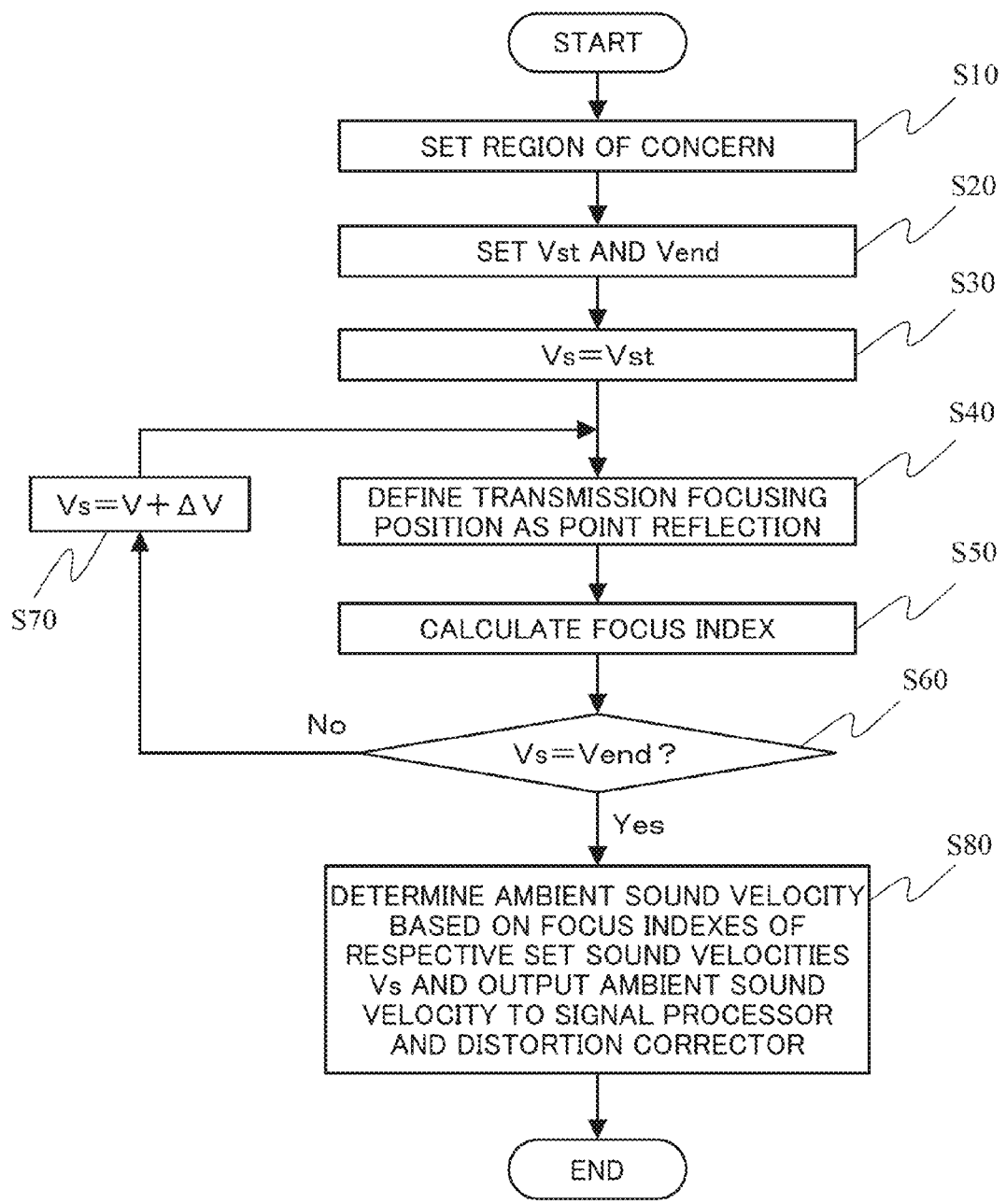
FIG. 4 is a flowchart showing the sequence of processing by the region-of-concern calculator shown in FIG. 3.

Next, the operation of the region-of-concern calculator 24 will be described with reference to the flowchart of FIG. 4. FIG. 4 is a flowchart showing the sequence of processing by the region-of-concern calculator 24 shown in FIG. 3.

As shown in FIG. 4, in the region-of-concern calculator 24, the region-of-concern setting section 60 sets a region of concern in accordance with the instruction from the controller 36 (Step S10).

In response to the setting of the region of concern, the transmission focusing control section 62 gives a transmission focusing instruction to the controller 36 so that the transmission circuit 14 performs the transmission focusing for the set region of concern.

Next, in the region-of-concern calculator 24, the set sound velocity specifying section 64 sets a start sound velocity Vst and end sound velocity Vend of a set sound velocity Vs (Step S20) and sets the start sound velocity Vst to the set sound velocity Vs (Step S30).

Set sound velocities Vs including the start sound velocity Vst and the end sound velocity Vend may be set in advance as default values. Alternatively, only the start sound velocity Vst and the end sound velocity Vend may be input by the operator as desired, while only the interval width therebetween (predetermined step sound velocity amount ΔV) may be set as a default value. Still alternatively, the operator may input the start sound velocity Vst, the end sound velocity Vend and the interval width as desired. When the set sound velocities Vs and the interval width are set as default values, various set sound velocities Vs may be set depending on the site to be observed, the sex or the like so that the operator can select an appropriate value.

In this example, it is assumed that the start sound velocity Vst is set to 1410 m/sec and the end sound velocity Vend is set to 1570 m/sec, and that based on the start sound velocity Vst and the end sound velocity Vend, the set sound velocity Vs is set at intervals of 40 m/sec which is the value of a predetermined interval width, for instance.

Figure 5:
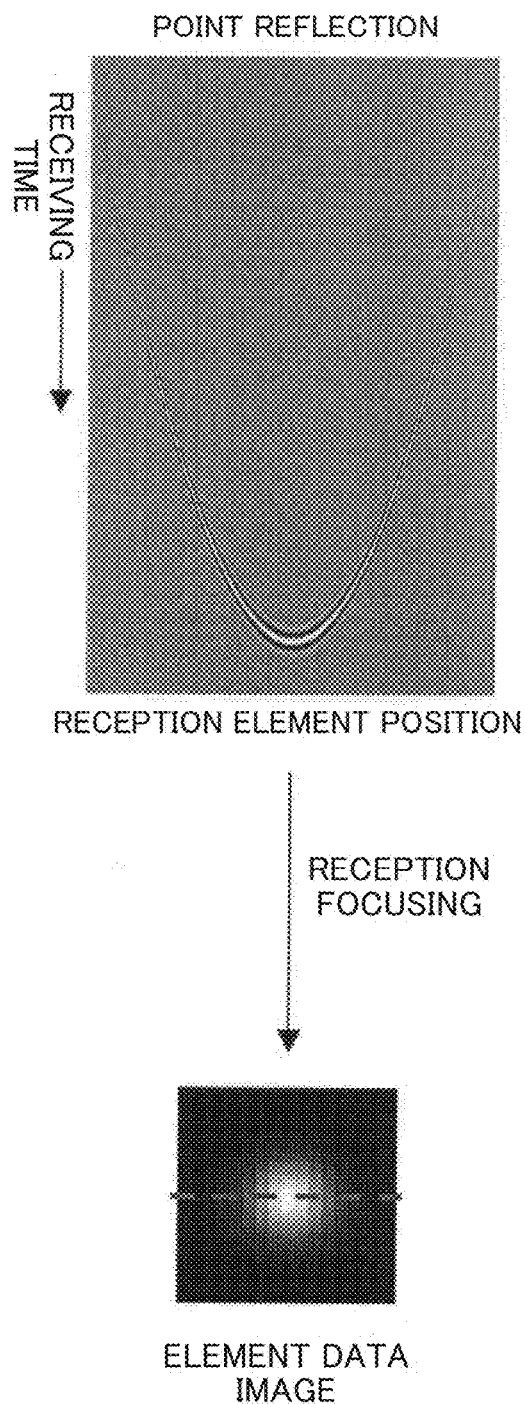
FIG. 5 is a diagram showing the state where reception focusing is performed on reception data from a point reflection.
Figure 6:
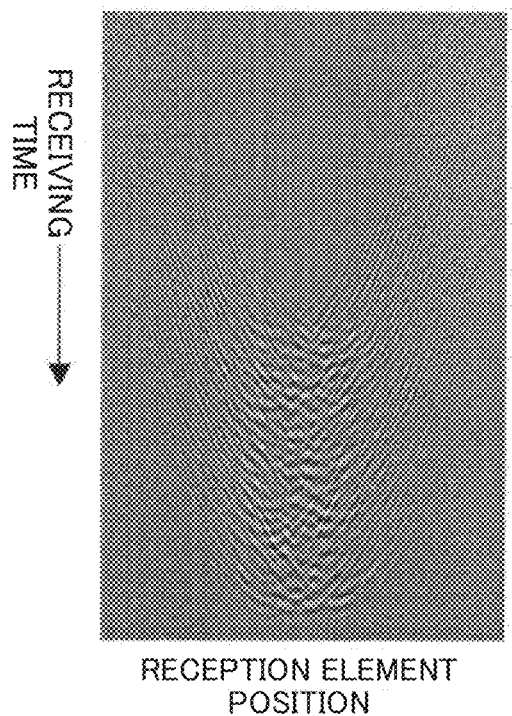
FIG. 6 is a diagram showing the state of countless scattering points in a speckle region.

As shown in FIG. 5, in the case of reception data from a point reflection, reception data which allows the analysis of intensity or sharpness can be obtained by performing the reception focusing. On the other hand, as shown in FIG. 6, in the case of countless scattering points in a speckle region, a peak value and a spatial frequency in the azimuth direction are disordered due to interference, so that it is difficult to obtain reception data which allows the analysis of intensity or sharpness in performing the reception focusing.

Figure 7:
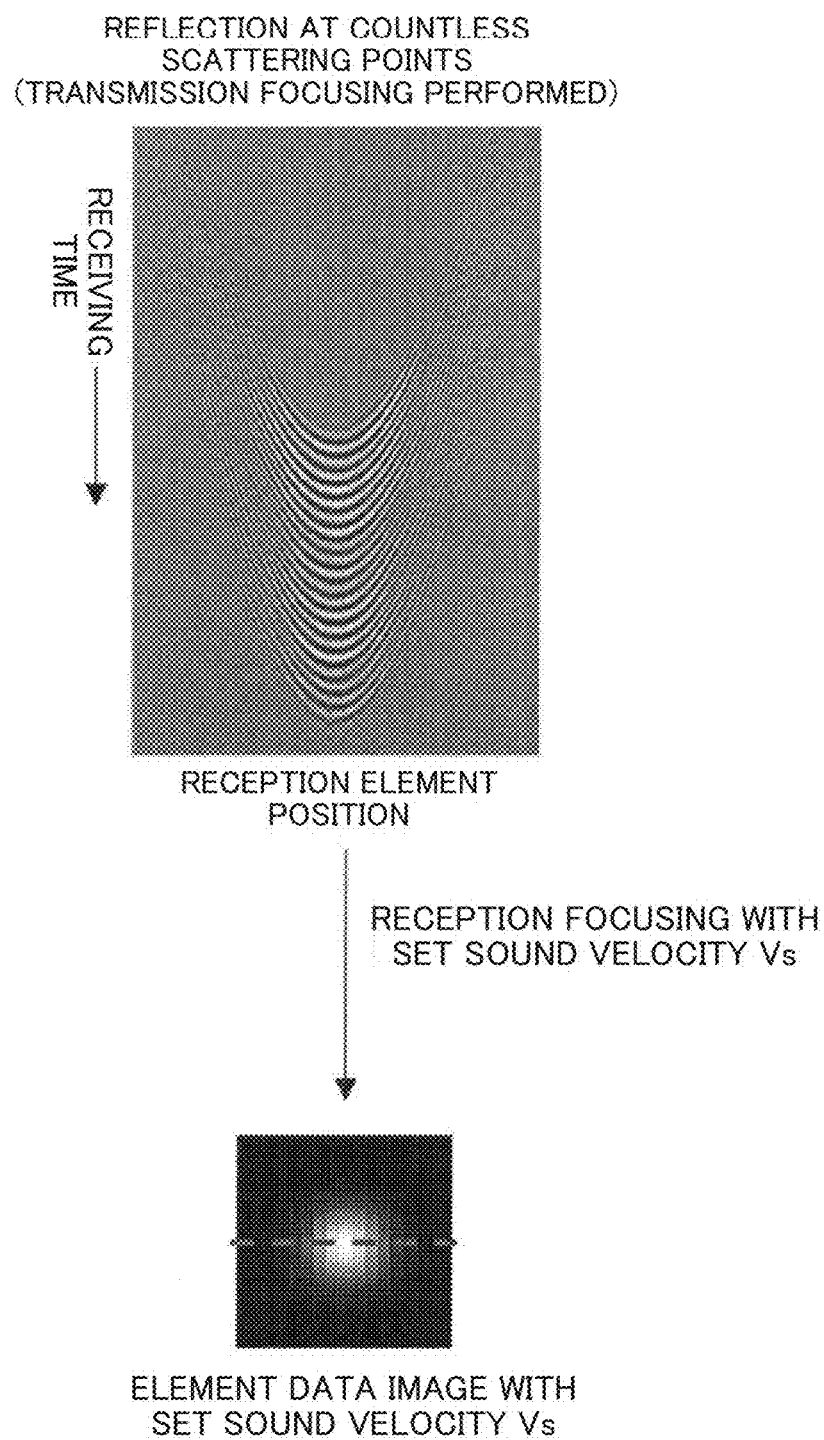
FIG. 7 is a diagram showing the state where a pseudo point reflection is formed by performing transmission focusing on countless scattering points in the speckle region.

To deal with it, as shown in FIG. 7, the region-of-concern calculator 24 forms a pseudo point reflection by performing the transmission focusing for the countless scattering points in the speckle region, performs the reception focusing on obtained reception data corresponding to an ultrasound transducer position, and determines an ambient sound velocity also in the speckle region in the same manner as the case of a point reflection which allows the analysis of intensity or sharpness.

In other words, in the region-of-concern calculator 24, the transmission focusing control section 62 gives a transmission focusing instruction to the controller 36 so that the transmission circuit 14 performs the transmission focusing for the region of concern set by the region-of-concern setting section 60, and defines a transmission focusing position as the pseudo point reflection (Step S40).

The focus index calculating section 66 of the region-of-concern calculator 24 reads out element data corresponding to a position whose ambient sound velocity is to be determined, i.e., a region of concern, from the element data memory 22 and performs the reception focusing on the element data for each of the plural set sound velocities Vs specified by the set sound velocity specifying section 64 to thereby calculate a focus index of the element data (Step S50).

The calculation of the focus index may be carried out by obtaining at least a part of element data directly from the reception circuit 16.

Figure 8:
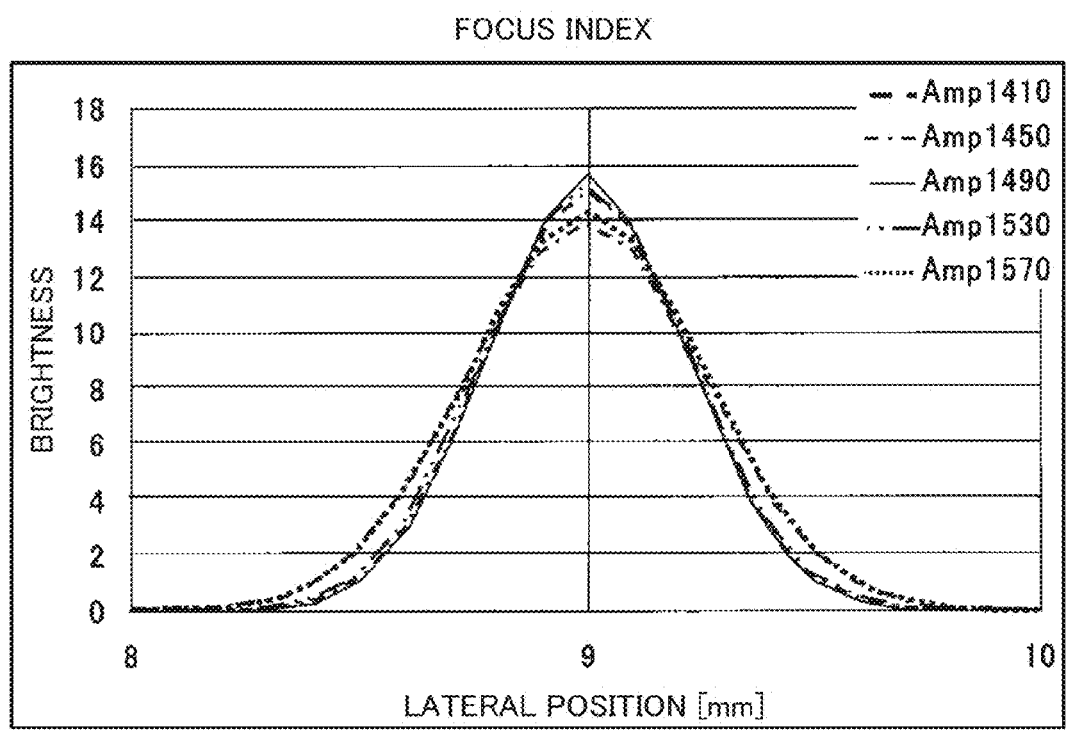
FIG. 8 is a graph showing focus indexes for respective set sound velocities.

While in the case of element data corresponding to the point reflection shown in FIG. 5, a tendency of variation depending on the set sound velocity Vs is observed in the peak value and the spatial frequency in the azimuth direction (lateral position) as shown in FIG. 8, the tendency shown in FIG. 8 is also observed in the case of element data acquired when a pseudo point reflection is formed by performing the transmission focusing as shown in FIG. 7.

Accordingly, the focus index calculating section 66 of the region-of-concern calculator 24 calculates an integration value, a square integration value, a peak value, a contrast value, a half width, a frequency spectral integration value, a frequency-spectral integration value or square integration value as normalized with its maximum value or a direct current component, an autocorrelation value and the like as focus indexes. For instance, in the case of FIG. 8, the focus index is the maximum at a set sound velocity of Amp 1490 m/sec.

Next, the set sound velocity specifying section 64 of the region-of-concern calculator 24 determines whether the set sound velocity Vs has reached the end sound velocity Vend (Step S60). As a result of the determination, when the set sound velocity Vs is lower than the end sound velocity Vend ("No" in Step S60), the set sound velocity specifying section 64 adds the predetermined step sound velocity amount ΔV, i.e., 40 m/sec in this example, to the set sound velocity Vs (Step S70), and the program returns to Step S40.

This routine is repeated and when the set sound velocity Vs is determined to have reached the end sound velocity Vend ("Yes" in Step S60), the procedure proceeds to Step S80.

In Step S80, the ambient sound velocity determining section 68 of the region-of-concern calculator 24 determines the ambient sound velocity at the region of concern based on the focus indexes of the plural set sound velocities Vs, for instance, by defining the set sound velocity with the highest focus index as the ambient sound velocity of the region of concern, and outputs the determined ambient sound velocity to the signal processor 46 and the distortion corrector 47. For instance, in the case of FIG. 8, the set sound velocity of Amp 1490 m/sec with the highest focus index is to be the ambient sound velocity.

In other words, the ambient sound velocity refers to an average sound velocity in a range between the ultrasound probe 12 (transducer array 42 (ultrasound transducers)) and a certain objective point when the sound velocity is assumed to be constant from the ultrasound probe 12 to the objective point.

As described above, the region-of-concern calculator 24 determines the ambient sound velocity for each of the set regions of concern.

Thus, the ultrasound diagnostic apparatus 10 performs the transmission focusing on the countless scattering points in the speckle region to form the pseudo point reflection, generates a focus index of each of the plural set sound velocities Vs and determines the ambient sound velocity of a region of concern based on the focus index of each of the plural set sound velocities Vs. Therefore, it is possible to properly determine the ambient sound velocity of a region of concern including the speckle region at the level of point reflection and thereby make a high-definition ultrasound image.

The method of determining the ambient sound velocity is not limited to the foregoing method and various known methods are suitable for use.

Next, the operation of the ultrasound diagnostic apparatus 10 will be explained to describe the distortion corrector 47 as well as the ultrasound diagnostic apparatus and data processing method of the present invention in detail.

The ultrasound diagnostic apparatus 10 has two operation modes of a live mode and an element data memory reproduction mode.

Figure 9:
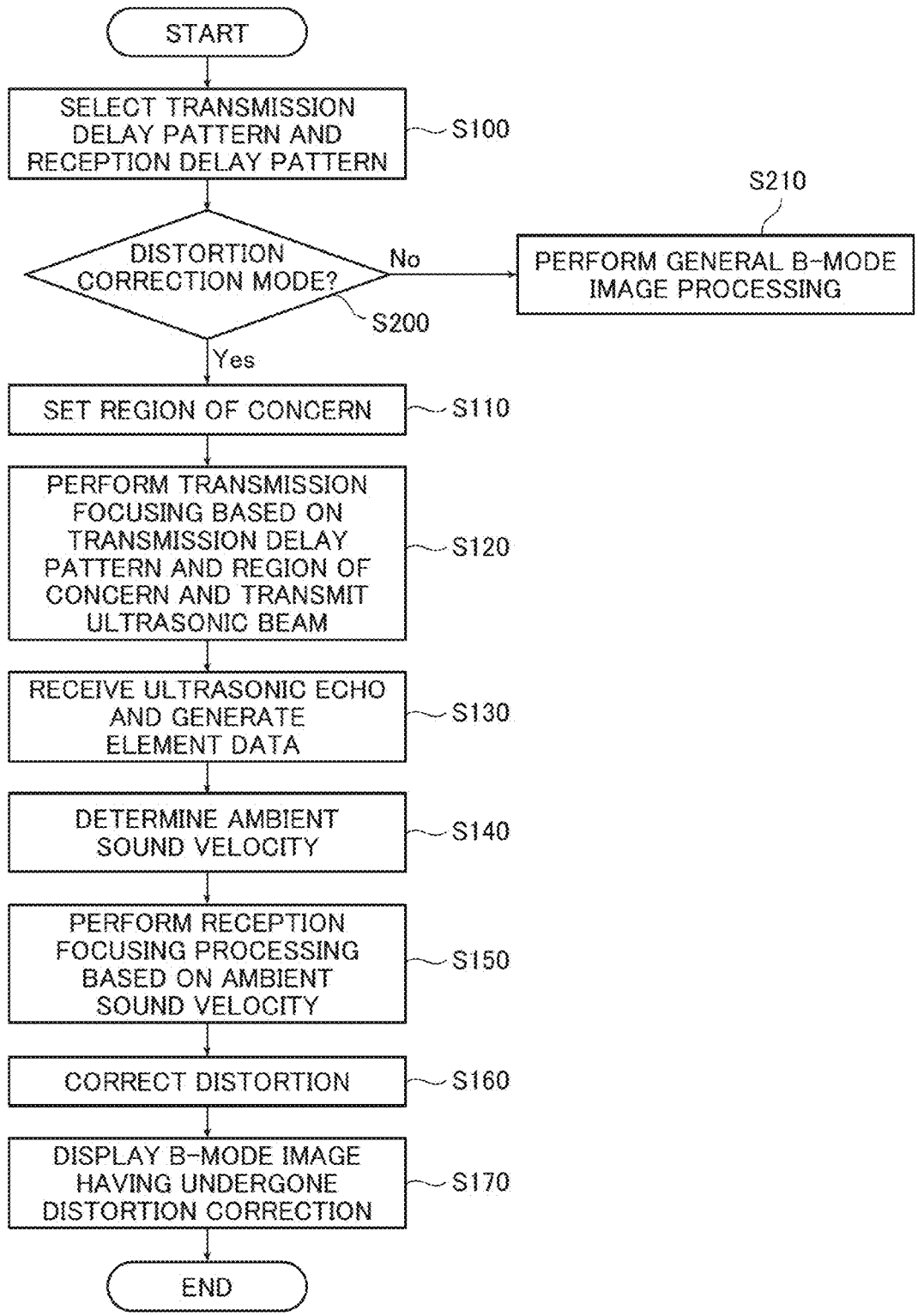
FIG. 9 is a flowchart showing the sequence of processing by the ultrasound diagnostic apparatus shown in FIG. 1 in a live mode.

The operation of the ultrasound diagnostic apparatus 10 in the live mode is first explained with reference to a flowchart shown in FIG. 9. FIG. 9 shows the flowchart of the sequence of processing by the ultrasound diagnostic apparatus shown in FIG. 1 in the live mode.

The live mode is a mode in which an ultrasound image (moving image) is obtained by transmitting and receiving ultrasonic waves with the ultrasound probe 12 being held in contact with a subject and the thus obtained image is displayed.

In the live mode, when the ultrasound probe 12 is caused to contact the subject and the operator inputs an instruction through the operating unit 38, the ultrasound examination starts.

When the ultrasound examination starts, the controller 36 sets transmission conditions and the like in accordance with the instruction input by the operator through the operating unit 38. Specifically, the controller 36 sets a transmitting direction of an ultrasonic beam and a receiving direction of an ultrasonic echo for each ultrasound transducer, selects a transmission delay pattern corresponding to the transmitting direction of an ultrasonic beam, selects a reception delay pattern corresponding to the receiving direction of an ultrasonic echo, and performs other operations (Step S100).

Furthermore, the controller 36 checks which has been selected, the reception focusing processing corresponding to ambient sound velocity (distortion correcting mode) or the reception focusing processing corresponding to reception delay pattern (Step S200). When the reception focusing processing corresponding to ambient sound velocity has been selected ("Yes" in Step S200), the controller 36 sends the set transmission conditions to the region-of-concern setting section 60 of the region-of-concern calculator 24. The region-of-concern setting section 60 sets regions of concern in accordance with the transmission conditions by dividing the whole extent of a B-mode image to be generated in a grid pattern as described above (Step S110). The transmission conditions include, for instance, a transmission interval of ultrasonic beams and the number of ultrasound transducers that perform transmission.

Furthermore, the region-of-concern setting section 60 gives an instruction to the transmission focusing control section 62 to perform the transmission focusing for the regions of concern.

The transmission focusing control section 62 gives a transmission focusing instruction to the controller 36 in accordance with the received instruction so that the transmission circuit 14 performs the transmission focusing for the set regions of concern.

The controller 36 outputs control signals to the transmission circuit 14 and the signal processor 46 based on the selected transmission delay patterns and reception delay patterns and the set regions of concern to thereby control the transmission and reception of ultrasonic waves.

When the reception focusing processing corresponding to reception delay pattern has been selected ("No" in Step S200), the controller 36 performs the transmission focusing processing corresponding to the selected transmission delay pattern and the reception focusing processing corresponding to the selected reception delay pattern to generate a B-mode image in the same manner as the generation of a general B-mode image. Therefore, in this case, the determination of the ambient sound velocity and the distortion correction by the distortion corrector 47 are not carried out (Step S210).

In accordance with the instruction on transmission focusing for the regions of concern, the transmission circuit 14 performs the transmission focusing on driving signals for the ultrasound transducers based on the selected transmission delay patterns and the regions of concern so as to cause the plural ultrasound transducers to transmit ultrasonic beams toward the subject (Step S120).

Then, ultrasonic echoes from the subject (ultrasonic wave reflection source) enter the plural ultrasound transducers. The ultrasound transducers output analog reception signals corresponding to the entered ultrasonic echoes to the reception circuit 16. The reception circuit 16 amplifies and A/D converts the analog reception signals supplied from the respective ultrasonic transducers to generate element data (digital reception signals) (Step S130).

The element data is supplied to the signal processor 46 of the image generator 18 and to the element data memory 22.

The element data memory 22 stores the supplied element data as well as information on a frame rate entered from the controller 36 in association with the element data.

On the other hand, in the region-of-concern calculator 24 that has set the regions of concern, the set sound velocity specifying section 64 sets the start sound velocity Vst and the end sound velocity Vend in accordance with the instruction from the controller 36 as described above, in parallel with the start of transmission of ultrasonic beams. Further, upon storage of the element data into the element data memory 22, the focus index calculating section 66 reads out the element data of each region of concern from the element data memory 22 and calculates the focus index, and subsequently, the ambient sound velocity determining section 68 determines the ambient sound velocity using the focus index (Step S140).

The ambient sound velocity determining section 68 supplies the determined ambient sound velocity to the signal processor 46 and the distortion corrector 47.

In the present invention, it is preferable to determine sound velocities at two or more regions of concern among the set regions of concern, and more preferable to determine sound velocities at two or more regions of concern in the depth direction and/or two or more regions of concern in the azimuth direction.

As described above, in this embodiment, it is particularly preferable to determine ambient sound velocities for each of the set regions of concern.

In the present invention, since the element data is stored in the element data memory 22, the element data as reception signals of ultrasonic echoes from the actual subject is available for use, which makes it possible to determine ambient sound velocities at such a large number of points.

The determination of the ambient sound velocity described above may be performed only one time when a region of concern is set (changed). Alternatively, the ambient sound velocity may be updated when an image greatly varies. Still alternatively, the ambient sound velocity may be updated every predetermined number of frames as appropriately set.

Once the ambient sound velocity is determined (Step S140) and supplied to the signal processor 46, the signal processor 46 performs the reception focusing processing using the ambient sound velocity as shown in FIG. 2, generates a B-mode image which has undergone the reception focusing processing having subjected to ambient sound velocity correction, and sends the B-mode image to the distortion corrector 47 (Step S150).

The distortion corrector 47 corrects distortion in the supplied B-mode image based on the supplied ambient sound velocities (Step S160).

For instance, in a B-mode image as conceptually shown in FIG. 11A, element data of a line I extending in the depth direction is data corresponding to times $t_1$, $t_2$, . . . as conceptually shown in FIG. 11B.

The signal processor 46 performs the reception focusing processing for each of times t1, t2, . . . with taking ambient sound velocities V into account to thereby generate a B-mode image. Since the unit of element data in terms of position is expressed by time, the signal processor 46 uses the ambient sound velocities V to convert time into distance (position) like $Vt_1/2$, $Vt_2/2$, . . . as conceptually shown in FIG. 11C to generate a B-mode image.

Ambient sound velocities at respective regions of concern and other regions in a subject often differ from each other depending on the position. In other words, there is an ambient sound velocity distribution in a subject. For example, when a blood vessel is observed, tissue positioned shallower than a blood vessel anterior wall, the inside of the blood vessel anterior wall and a vascular lumen have different ambient sound velocities.

Therefore, the arrival time of an ultrasonic echo from a reflection point to an ultrasound transducer varies depending on the ambient sound velocity at a position in the subject.

Conventional ultrasound diagnostic apparatuses, however, each generate a B-mode image solely using a single ambient sound velocity V. and consequently, the B-mode image is distorted relative to the actual subject.

In contrast, in the ultrasound diagnostic apparatus 10 of the invention, the image generator 18 has the distortion corrector 47 that performs coordinate transformation based on ambient sound velocities to thereby correct distortion in a B-mode image caused due to a sound velocity distribution.

To be more specific, the distortion corrector 47 first performs coordinate transformation with respect to each of times t1, t2, respective pixels conceptually shown in FIG. 10A in a B-mode image generated by the signal processor 46 with the use of ambient sound velocities V1, V2 . . . at respective regions of concern at which the respective pixels (respective sampling points) are located correspondingly. For instance, as conceptually shown in FIG. 10B, time t is converted into distance like $V_1t_1/2$, $V_2t_2/2$, . . . to thereby generate a brightness image.

At this time, since there is an ambient sound velocity distribution in the subject, pixels (sampling points) of the generated brightness image are to be arranged at different intervals as shown in FIG. 10B.

To deal with it, the distortion corrector 47 performs interpolation to thereby generate a B-mode image having undergone the distortion correction so that the pixels of the B-mode image are arranged at constant intervals, as conceptually shown in FIG. 10C.

According to the present invention, therefore, it is possible to generate a high-quality ultrasound image not having distortion to be caused due to an ambient sound velocity distribution in a subject and hence, more accurate diagnosis can be carried out using ultrasound images.

The method of interpolation performed by the distortion corrector 47 is not particularly limited, and various known interpolation methods including linear interpolation and spline interpolation can be used.

When available ambient sound velocities are ones corresponding to not all but a part of pixels of a B-mode image generated by the signal processor 46, the ambient sound velocity of a pixel (sampling point) may be determined by interpolating ambient sound velocities at peripheral pixels (peripheral regions of concern). In this case, either of the region-of-concern calculator 24 and the distortion corrector 47 may perform the determination of an ambient sound velocity by interpolation.

Further, in the ultrasound diagnostic apparatus of the invention, the signal processor 46 generating a B-mode image may have the function of the distortion corrector 47.

Specifically, after ambient sound velocities are supplied to the signal processor 46, the signal processor 46 may calculate the distance of pixels (sampling points) using the ambient sound velocities corresponding to the pixels at the time of time-distance conversion in generating a B-mode image, thereby generating a brightness image, and perform interpolation suitable for the pixels of the B-mode image, thus generating a B-mode image.

The distortion corrector 47 supplies to the DSC 48 the B-mode image having undergone the distortion correction performed based on the ambient sound velocities.

The DSC 48 converts the B-mode image into an image signal of, for instance, television method and supplies the image signal to the image processor 50. The image processor 50 performs predetermined processing on the supplied B-mode image.

The B-mode image processed by the image processor 50 is stored in the image memory 52 and also displayed on the monitor 34 under the control of the display controller 32. Thus, the B-mode image having undergone the distortion correction is displayed on the monitor 34 (Step S170).

When a freeze button is pressed during display of a B-mode image in the above-described live mode, a B-mode image displayed at the time of pressing the freeze button is displayed as a still image on the monitor 34.

This enables the operator to observe the B-mode image in detail through the still image.

Next, the operation of the ultrasound diagnostic apparatus 10 in the element data memory reproduction mode is explained.

The element data memory reproduction mode is a mode in which an ultrasound image is displayed based on reception data stored in the element data memory 22.

Upon input of an instruction through the operating unit 38, the controller 36 switches the operation mode of the ultrasound diagnostic apparatus 10 into the element data memory reproduction mode.

In the element data memory reproduction mode, the controller 36 reads out reception data from the element data memory 22 and transmits the reception data to the signal processor 46 of the image generator 18. The subsequent operation is the same as that in the live mode. As a result, an ultrasound image (moving image or still image) based on the reception data stored in the element data memory 22 is displayed on the monitor 34.

While the ultrasound diagnostic apparatus and data processing method of the present invention have been described above in detail, the invention is by no means limited to the above embodiments, and various improvements and modifications may be made without departing from the scope and spirit of the invention.

What is claimed is:

1. An ultrasound diagnostic apparatus, comprising:
an ultrasound probe having ultrasound transducers each of which transmits an ultrasonic wave, receives an ultrasonic echo reflected by a subject and outputs an analog reception signal in accordance with the ultrasonic echo as received;
a transmission and reception controller that causes the ultrasound probe to transmit and receive the ultrasonic waves;
an analog-to-digital converter that analog-to-digital converts the analog reception signal output by each of the ultrasound transducers into digital reception signals;
an element data memory that stores the digital reception signals;
a region-of-concern calculator that determines a sound velocity at each of plural points in the subject by using the digital reception signals converted by the analog-to-digital converter or the digital reception signals read out from the element data memory;
a signal processor that generates a brightness image of the subject by performing reception focusing processing on the digital reception signals converted by the analog-to-digital converter or the digital reception signals read out from the element data memory; and
a coordinate transformer that performs coordinate transformation on the brightness image generated by the signal processor based on the sound velocity at each of the plural points determined by the region-of-concern calculator,
wherein the region-of-concern calculator includes a region-of-concern setter that sets at least one region of concern; a set sound velocity specifying section that sets a plurality of set sound velocities for use in performing reception focusing on digital reception signals of the at least one region of concern; and a focus index calculating section that calculates a focus index of a brightness image at the at least one region of concern by performing the reception focusing on digital reception signals of the at least one region of concern for each of the plurality of set sound velocities,
wherein the focus index calculating section calculates at least one of an integration value, a square integration value, a peak value, a contrast value, a half width, a frequency spectral integration value, a frequency-spectral integration value or square integration value as normalized with a maximum value or a direct current component, and an autocorrelation value as the focus index,
wherein the transmission and reception controller causes the ultrasound probe to transmit and receive ultrasonic waves corresponding to the at least one region of concern as set,
wherein the region-of-concern calculator determines, as the sound velocity of the at least one region of concern, a set sound velocity with a highest focus index from among focus indexes of the plural set sound velocities as set,
wherein the coordinate transformation performed by the coordinate transformer is time-distance conversion that multiplies each of sound velocities of respective pixels in the at least one region of concern on the brightness image by each of times of the respective pixels to convert time into distance,
wherein the coordinate transformer performs interpolation on pixels in a brightness image having undergone the coordinate transformation to thereby generate a corrected image having pixel positions corresponding to those of the brightness image generated by the signal processor, and
wherein the coordinate transformer and the region-of-concern calculator, including the region-of-concern setter, the set sound velocity specifying section and the focus index calculating section, are constituted by a computer and operation programs for causing the computer to perform processing functions associated with the region-of-concern calculator and the coordinate transformer or by a digital circuitry.

2. The ultrasound diagnostic apparatus according to claim 1, wherein the signal processor performs the reception focusing processing using the sound velocity determined by the region-of-concern calculator.

3. The ultrasound diagnostic apparatus according to claim 1, wherein the region-of-concern setter sets regions of concern at two or more points in a depth direction and/or at two or more points in an azimuth direction.

4. The ultrasound diagnostic apparatus according to claim 1,
wherein the region-of-concern setter sets two or more regions of concern, and
wherein the region-of-concern calculator determines a sound velocity at each of the two or more of the regions of concern set by the region-of-concern setter.

5. An ultrasound diagnostic apparatus comprising:
an ultrasound probe having ultrasound transducers each of which transmits an ultrasonic wave, receives an ultrasonic echo reflected by a subject and outputs an analog reception signal in accordance with the ultrasonic echo as received;
a transmission and reception controller that causes the ultrasound probe to transmit and receive the ultrasonic waves;
an analog-to-digital converter that analog-to-digital converts the analog reception signal output by each of the ultrasound transducers into digital reception signals;
an element data memory that stores the digital reception signals;
a region-of-concern calculator that determines a sound velocity at each of plural points in the subject by using the digital reception signals converted by the analog-to-digital converter or the digital reception signals read out from the element data memory;
a signal processor that generates a brightness image of the subject by performing reception focusing processing on the digital reception signals converted by the analog-to-digital converter or the digital reception signals read out from the element data memory; and
a coordinate transformer that performs coordinate transformation on the brightness image generated by the signal processor based on the sound velocity at each of the plural points determined by the region-of-concern calculator,
wherein the region-of-concern calculator includes a region-of-concern setter that sets at least one region of concern; a set sound velocity specifying section that sets a plurality of set sound velocities for use in performing reception focusing on digital reception signals of the at least one region of concern; and a focus index calculating section that calculates a focus index of a brightness image at the at least one region of concern by performing the reception focusing on digital reception signals of the at least one region of concern for each of the plurality of set sound velocities, wherein the focus index calculating section calculates at least one of an integration value, a square integration value, a peak value, a contrast value, a half width, a frequency spectral integration value, a frequency-spectral integration value or square integration value as normalized with a maximum value or a direct current component, and an autocorrelation value as the focus index, the transmission and reception controller causes the ultrasound probe to transmit and receive ultrasonic waves corresponding to the at least one region of concern as set, wherein the region-of-concern calculator determines, as the sound velocity of the at least one region of concern, a set sound velocity with a highest focus index from among focus indexes of the plural set sound velocities as set, wherein the coordinate transformation performed by the coordinate transformer is time-distance conversion that multiplies each of sound velocities of respective pixels in the at least one region of concern on the brightness image by each of times of the respective pixels to convert time into distance, wherein the region-of-concern calculator sets a region of concern corresponding to each of all pixels of the brightness image generated by the signal process to determine a sound velocity corresponding to each of all pixels of the brightness image, and wherein the coordinate transformer and the region-of-concern calculator, including the region-of-concern setter, the set sound velocity specifying section and the focus index calculator section, are constituted by a computer and operation programs for causing the computer to perform processing functions associated with the region-of-concern calculator and the coordinate transformer or by a digital circuitry.

6. A data processing method, comprising:
a step of obtaining analog reception signals, each corresponding to a respective ultrasonic echo reflected by a subject by transmitting an ultrasonic wave to the subject;
a step of analog-to-digital converting the analog reception signals into a digital reception signals;
a step of storing the digital reception signals;
a step of determining a sound velocity at each of plural points in the subject by using the digital reception signals as analog-to-digital converted or the digital reception signals as stored;
a step of generating a brightness image of the subject by performing reception focusing processing on the digital reception signals as analog-to-digital converted or the digital reception signals as stored; and
a step of performing coordinate transformation on the brightness image as generated based on the sound velocity at each of the plural points as determined,
wherein the step of determining a sound velocity sets at least one region of concern,
wherein the step of obtaining analog reception signals transmits and receives ultrasonic waves corresponding to the at least one region of concern as set,
wherein the step of determining a sound velocity includes a step of setting a plurality of set sound velocities for use in performing reception focusing on digital reception signals of the at least one region of concern; a step of calculating a focus index of a brightness image at the region of concern by performing the reception focusing on digital reception signals of the at least one region of concern for each of the plurality of set sound velocities; and a step of determining, as the sound velocity of the at least one region of concern, a set sound velocity with a highest focus index from among focus indexes of the plural set sound velocities as set, wherein the step of calculating a focus index calculates at least one of an integration value, a square integration value, a peak value, a contrast value, a half width, a frequency spectral integration value, a frequency-spectral integration value or square integration value as normalized with a maximum value or a direct current component, and an autocorrelation value as the focus index, wherein the coordinate transformation is time-distance conversion that multiplies each of sound velocities of respective pixels in the at least one region of concern on the brightness image by each of times of the respective pixels to convert time into distance, and wherein the step of performing coordinate transformation generates a corrected image having pixel positions corresponding to those of a brightness image generated by the step of generating a brightness image by performing interpolation on pixels in the brightness image having undergone the coordinate transformation.

7. The data processing method according to claim 6, wherein in the step of generating a brightness image of the subject, the reception focusing processing is performed using the sound velocity as determined.

8. The data processing method according to claim 6, wherein in the step of setting at least one region of concern, regions of concern are set at two or more points in a depth direction and/or at two or more points in an azimuth direction.

9. The data processing method according to claim 6,
wherein in the step of setting at least one region of concern, two or more regions of concern are set, and
wherein in the step of determining a sound velocity, a sound velocity is determined at each of the two or more of the regions of concern as set.

10. A data processing method comprising:
a step of obtaining analog reception signals each corresponding to a respective ultrasonic echo reflected by a subject by transmitting an ultrasonic wave to the subject;
a step of analog-to-digital converting the analog reception signals into digital reception signals;
a step of storing the digital reception signals;
a step of determining a sound velocity at each of plural points in the subject by using the digital reception signals as analog-to-digital converted or the digital reception signals as stored;
a step of generating a brightness image of the subject by performing reception focusing processing on the digital reception signals as analog-to-digital converted or the digital reception signals as stored; and
a step of performing coordinate transformation on the brightness image as generated based on the sound velocity at each of the plural points as determined,
wherein the step of determining a sound velocity sets at least one region of concern, wherein the step of obtaining analog reception signals transmits and receives ultrasonic waves corresponding to the at least one region of concern as set, wherein the step of determining a sound velocity includes a step of setting a plurality of set sound velocities for use in performing reception focusing on digital reception signals of the at least one region of concern; a step of calculating a focus index of a brightness image at the at least one region of concern by performing the reception focusing on digital reception signals of the at least one region of concern for each of the plurality of set sound velocities; and a step of determining, as the sound velocity of the at least one region of concern, a set sound velocity with a highest focus index from among focus indexes of the plural set sound velocities as set, wherein the step of calculating a focus index calculates at least one of an integration value, a square integration value, a peak value, a contrast value, a half width, a frequency spectral integration value, a frequency-spectral integration value or square integration value as normalized with a maximum value or a direct current component, and an autocorrelation value as the focus index, wherein the coordinate transformation is time-distance conversion that multiplies each of sound velocities of respective pixels in the at least one region of concern on the brightness image by each of times of the respective pixels to convert time into distance, and wherein in the step of determining a sound velocity, a region of concern corresponding to each of all pixels of the brightness image as generated is set and a sound velocity corresponding to each of all pixels of the brightness image is determined.

\* \* \* \* \*